(12) United States Patent
Schuren et al.

(10) Patent No.: US 10,596,164 B2
(45) Date of Patent: Mar. 24, 2020

(54) **ANTI-*CLOSTRIDIUM* COMPOUNDS**

(71) Applicant: Nederlandse Organisatie voor toegepast-natuurwetenschappelijk Onderzoek TNO, s-Gravenhage (NL)

(72) Inventors: Frank Henri Johan Schuren, The Hague (NL); Roy Christiaan Montijn, The Hague (NL)

(73) Assignee: Nederlandse Organisatie voor toegepast-natuurwetenschappelijk Onderzoek TNO, 's-Gravenhage (NL)

( * ) Notice: Subject to any disclaimer, the term of this patent is extended or adjusted under 35 U.S.C. 154(b) by 0 days.

(21) Appl. No.: 15/304,456

(22) PCT Filed: Apr. 14, 2015

(86) PCT No.: PCT/NL2015/050248
§ 371 (c)(1),
(2) Date: Oct. 14, 2016

(87) PCT Pub. No.: WO2015/160251
PCT Pub. Date: Oct. 22, 2015

(65) Prior Publication Data
US 2017/0035750 A1    Feb. 9, 2017

(30) Foreign Application Priority Data
Apr. 15, 2014    (EP) .................................... 14164707

(51) Int. Cl.
*A61K 31/4745*    (2006.01)

(52) U.S. Cl.
CPC ............................... *A61K 31/4745* (2013.01)

(58) Field of Classification Search
CPC .......................... A61K 31/122; A61K 31/4745
See application file for complete search history.

(56) References Cited

U.S. PATENT DOCUMENTS

2004/0116493 A1 *  6/2004  Sugimori ............. C07D 471/06
                                                            514/389

FOREIGN PATENT DOCUMENTS

EP          1 340 755       9/2003
WO       WO-03/095453     11/2003

OTHER PUBLICATIONS

Antunes Rossana et al, Rev. bras. Pharmacogn. vol. 16 No. 4 João Pessoa Oct./Dec. 2006.*
Miller et al, Bioorganic & Medicinal Chemistry 9 (2001) 2015-2024.*
Public Health Agency of Canada, Fact Sheet-Clostridium difficile (C. difficile), Mar 13, 2014.*
Segreti, Clin Microbiol Infect 2009; I5 (Suppl. 6) 5-10 (Year: 2009).*
Antunes et al., "Atividade antimicrobiana "in vitro" e determinação da concentração inhibitória mínina (CIM) de fitoconstituintes e produtos sintéticos sobre bactérias e fungos leveduriformes," Brazilian Journal of Pharmacology (2006) 16(4):517-524.
International Search Report and Written Opinion for PCT/NL2015/050248, dated Jul. 14, 2015, 10 pages.
Miller et al., "The Synthesis and Screening of 1,4,5,8-Napthalenetetracarboxylic Diimide-Peptide Conjugates with Antibacterial Activity," Bioorganic & Medicinal Chemistry (2001) 9:2015-2024.
Schütz et al., "Basisch alkylierte Imide der Naphthalin-1,4,5,8-tetracarbonsäure and ihre chemotherapeutischen Eigenschaften," Arzneimittel Forschung, Drug Research (1971) 21(6):739-763.

* cited by examiner

*Primary Examiner* — Jean P Cornet
(74) *Attorney, Agent, or Firm* — Morrison & Foerster LLP

(57) ABSTRACT

The present invention relates to compounds having a backbone structure for use as antibiotic, more specifically use against infections with Gram positive bacteria, preferably *Clostridium*, more preferably *C. dfficile* or *C. perfringens*. The compounds of the invention are particularly useful against spores of these bacteria.

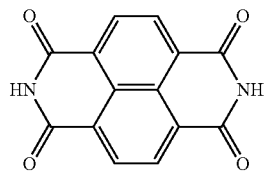

17 Claims, No Drawings

ANTI-*CLOSTRIDIUM* COMPOUNDS

CROSS-REFERENCE TO RELATED APPLICATIONS

This application is the national phase of PCT application PCT/NL2015/050248 having an international filing date of 14 Apr. 2015, which claims benefit of European patent application No. 14164707.3 filed 15 Apr. 2014. The contents of the above patent applications are incorporated by reference herein in their entirety.

FIELD OF THE INVENTION

The present invention relates to antibiotic compounds, more specifically compounds that are useful to combat *Clostridium*, more particularly *C. difficile*.

BACKGROUND OF THE INVENTION

Several species of *Clostridium* are important to human and animal health. *C. difficile, C. perfringens* and *C. botulinium* are commonly known food-contaminating bacteria. The *Clostridium* bacterium is able to form spores and these spores are able to survive under various conditions. Under some conditions *Clostridium difficile* bacteria can outgrow and outnumber the normal gut microbiota. Such a condition can be very harmful, causing loss of appetite, diarrhea, abdominal pain and edema of the intestine. This can develop into pseudomembraneous colitis and in rare cases in toxic megacolon. Treatment for *C. difficile* can be difficult due to its ability as a spore to survive classical antibiotic treatment, which is performed with vancomycin and/or metronidazole. Also a recently introduced antibiotic, fidaxomycin, seems not be active against *C. difficile* spores. Currently the best approach is via fecal transplantation, where the gut content is replaced by that of a healthy individual. Of course, such a fecal transplantation is more costly, since this has to be performed under close medical surveillance.

The abundance of *C. difficile* infections has been increasing in the last decades. Infection with this bacterium is the most abundant bacterial infection in health care institutions. Thus, adequate treatment for infections of *C. difficile*, which especially also affects the spores of *C. difficile*, is urgently needed.

Next to *C. difficile* other *Clostridum* species are known for their toxic effects. *C. perfringens* is a Gram-positive square-ended anaerobic (microaerophilic) *bacillus* classified in Group III of the Family Bacillaceae. This non-motile member of the clostridia forms oval, central spores rarely seen in culture unless grown in specially formulated media, although the spores are produced readily in the intestine. Capsules may be seen in smears from tissue. Nitrate is reduced and lecithinase (alpha-toxin activity) can be demonstrated in egg yolk medium (Nagler reaction). Sugar reactions (acid and gas) may be irregular. Food poisoning from *C. perfringens* gives rise to abdominal pain, nausea and acute diarrhea 8-24 h after the ingestion of large numbers of the organism, a proportion of which survive the acid conditions of the stomach (Sutton & Hobbs, 1971). The illness is usually brief and full recovery within 24-48 h is normal. However, death occasionally occurs in the elderly or otherwise debilitated patients, e.g. in hospitals or institutions (Smith, 1998). The symptoms of the disease are caused by an enterotoxin. *C. perfringens* is grouped into 5 types A-E according to the exotoxins (soluble antigens) produced. Types A, C and D are pathogens for humans, types B, C, D and E, and possibly A also, affect animals. The enterotoxin produced by types A and C is distinct from the exotoxins and is responsible for the acute diarrhea that is the predominant symptom of *C. perfringens* food poisoning. The beta-toxin of type C appears to be the necrotic factor in the disease enteritis necroticans jejunitis ("pig-bel"). Type A strains are responsible for gas gangrene (myonecrosis), necrotizing colitis, peripheral pyrexia, septicemia as well as food poisoning.

Botulinum neurotoxin (BoNT) from *C. botulinium* has the capacity to cause disease in essentially all vertebrates. Symptoms may appear in a few hours or take several days to appear. Initial symptoms such as weakness, fatigue and vertigo, are usually followed by blurred vision and progressive difficulty in speaking and swallowing. In type E botulism nausea and vomiting often occur early in the illness and probably contribute to its lower mortality than types A and B. Disturbed vision and difficulty in speaking and swallowing are due to neurological implications involving extra-ocular and pharynx muscles. Weakening of diaphragm and respiratory muscles also occurs and death is usually due to respiratory failure. Specifically neurotransmission of the peripheral nerve system is blocked. The mortality rate has fallen due to early diagnosis, prompt administration of antitoxin, and artificial maintenance of respiration. The illness is serious and full recovery usually takes many months.

*C. tetanus* causes one of the major diseases still present in developing countries, tetanus. Tetanus has been known to take up to ten years to manifest, but normally, incubation period is a few days to a few weeks. The first signs of the disease include mild muscle contractions at the site of infection as the infection gradually spreads along nerve fibers to the spinal cord and brain stem. Trismus (lockjaw) ensues with continued rigidity and spasms of the extremities. Death occurs when spasms interfere with respiration.

*Clostridium* belongs to the Gram-positive bacteria, of which many are known as pathogens. Examples of those pathogenic Gram-positive bacteria are the spore forming *Bacillus* species, the non-spore-forming bacilli *Corynebacterium* and *Listeria* and the sphere-shaped *Streptococcus* and *Staphylococcus*. Especially the latter one, of which *S. aureus* is the most common representative often give lead to bacteria that are multi-resistant (MRSA). Accordingly, new antibiotics that can be used against these bacteria are urgently needed.

SUMMARY OF THE INVENTION

The present inventors have found new antibiotic compounds that are capable of combatting bacteria, preferably gram-positive bacteria, specifically *Clostridium*, more specifically *C. difficile* and which also are effective against the spores of *C. difficile*.

Accordingly, the present invention relates to compounds having a backbone structure for use as antibiotic, more specifically use against infections with Gram positive bacteria, preferably *Clostridium*, more preferably *C. difficile* or *C. perfringens*. The compounds of the invention are particularly useful against spores of these bacteria. It further appeared that also compounds in which the nitrogens in the above formula are replaced by carbon atoms are effective.

DETAILED DESCRIPTION

Definitions

The term "alkyl" refers to a straight or branched alkyl radical containing one to six carbon atoms including, but not limited to, methyl, ethyl, propyl, isopropyl, n-butyl, t-butyl and neopentyl. The term "alkyl" includes partially unsaturated alkyl groups, such as alkenyl and alkynyl moieties, which refer to $C_{1-6}$ linear or branched alkenyl and $C_{1-6}$ linear or branched alkynyl, respectively. An alkyl group may be substituted as elsewhere defined.

The term "hydroxyalkyl" refers to an alkyl moiety as defined above in which one or more of the carbon atoms is substituted with a hydroxyl (—OH) group. An hydroxyalkyl group may be substituted as elsewhere defined.

The term "alkoxy" refers to an alkyl group as previously defined, i.e. with one to six carbon atoms, attached to a parent molecular moiety by a heteroatom linkage (—O—, —S—, or —N=), and therefore includes, for the scope of the present invention, thioethers and secondary or tertiary amines. The term "alkoxy" preferably refers to an alkyl group which is coupled to the parent molecular moiety by an ether (—O—) linkage. An alkoxy group may be substituted as elsewhere defined.

The term "alkoxyalkyl" refers to a $C_{1-8}$ alkyl group in which one or more of the carbon atoms has been replaced by an oxygen atom. The term "alkoxyalkyl" includes, for the scope of the present invention, the terms "alkylamine" and "alkylthioether", which refer to a $C_{1-8}$ alkyl (including alkenyl or alkynyl) group in which one or more of the carbon atoms has been replaced by an amine, a thioether or thiol group, respectively, or structures which include combinations of said features. Preferably, the term alkoxyalkyl refers to a $C_{1-8}$ alkyl group in which one or more of the carbon atoms has been replaced by an oxygen atom. An alkoxyalkyl group may be substituted as elsewhere defined.

The term "carbocycle" or "carbocyclic group" refers to a mono-, bi- or tricyclic moiety, which may be aromatic or non-aromatic, or a combination of these. Examples include aryl, naphthyl, anthracyl, indanyl and cycloalkyl. Preferably, the one or more ring structures in a carbocycle comprise a 5- to 7-membered ring, in particular a 6-membered ring. Preferably, a carbocyclic group is aryl or cycloalkyl, more preferably aryl. A carbocycle may be substituted as elsewhere defined, and the carbocyclic group may be attached through an alkyl, alkoxy or alkoxyalkyl spacer.

The term "heterocycle" or "heterocyclic group", as used herein, refers to mono- or bicyclic aromatic and non-aromatic heterocycles comprising one or more of S, N and/or O as heteroatoms. A heterocycle may be substituted as elsewhere defined, and the heterocycle may be attached through an alkyl, alkoxy or alkoxyalkyl spacer.

The term "cycloalkyl" refers to saturated or unsaturated monocyclic radicals of three to eight carbon atoms. Examples include cyclopropyl, cyclobutyl, cyclopentyl, cyclopentenyl, cyclohexyl, cyclohexenyl, cycloheptyl and cyclooctyl. A cycloalkyl group may be substituted as elsewhere defined, and the cycloalkyl group may be attached through an alkyl, alkoxy or alkoxyalkyl spacer.

The term "aryl" refers to substituted or unsubstituted monocyclic aromatic hydrocarbons. Examples include phenyl, toluyl, xylyl and methoxyphenyl. An aryl group may be attached through an alkyl, alkoxy or alkoxyalkyl spacer.

The term "halogen" as used herein refers to one of the group consisting of F, Cl, Br and I, preferably F.

The term "substituted" as used herein refers to the presence on a moiety of a hydroxy-, thiol-, thioether, amine-, secondary amine-, tertiary amine-, nitro-, cyano-, isocyano-, halogen, oxo-, carboxylic acid, alkyl-, hydroxyalkyl-, alkoxy-, alkoxyalkyl-, a carbocyclic- or a heterocyclic group.

Examples of a substituted alkyl group are —C(O)CH$_3$, —CH$_2$(NO$_2$)HCH$_3$, and —CH$_2$CH$_2$CN. Examples of a substituted alkoxygroup are —OCH$_2$F, —OCH$_2$CH$_2$CH$_2$CH(OH)CH$_3$ and —OCH$_2$-cyclohexyl. Examples of a substituted alkoxyalkylgroup include —OCH$_2$OCH$_3$, —C(O)OCH$_3$, and CH$_2$CH$_2$CH(OH)CH=CH$_2$.

The term "pharmaceutically acceptable salts" as used herein refers to those carboxylate salts, esters, and prodrugs of the compound of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention.

Pharmaceutically acceptable salts are well known in the art and refer to the relatively non-toxic, inorganic and organic acid addition salts of the compounds of the present invention. For example, S. M. Berge et al. describe pharmaceutically acceptable salts in detail in J. Pharmaceutical Sciences, 66: 1-19 (1977) which is incorporated herein by reference. The salts can be prepared in situ during the final isolation and purification of the compounds of the invention, or separately by reacting the free base function with a suitable organic acid.

Examples of pharmaceutically acceptable, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, stearate, succinate, sulphate, tartrate, thiocyanate, p-toluenesulphonate, undecanoate, valerate salts, and the like. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate. sulphate, phosphate, nitrate, loweralkyl sulphonate and aryl sulphonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The term "pharmaceutically acceptable solvate" represents an aggregate that comprises one or more molecules of the solute, such as a compound of the invention, with one or more molecules of solvent.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A. C. S. Symposium Series, and in Edward B. Roche, ed., Bioreversible Carriers in Drug Design, American Pharmaceutical Association and Pergamon Press, 1987, both of which are incorporated herein by reference.

The invention relates to compounds that have proven to be effective against Gram-positive bacteria and especially against *Clostridum difficile* or *C. perfringens*. Accordingly, they can be used for antibiotic treatment.

Compounds having a

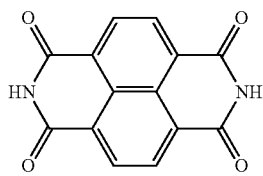 [SMILES: O=C1NC(=O)c2ccc3c4c(ccc1c24)C(=O)NC3=O]

backbone structure are known from US 2004/0116493 where they have been identified as compounds active against the Gram-negative *Helicobacter*. However, such compounds were found not to be active against other (pathogenic) bacteria, such as *Escherichia coli, Pseudomonas aeruginosa, Klebsiella pneumonia, Streptococcus pneumonia, Enterococcus faecalis* and *Staphylococcus aureus*.

It is thus surprising that the compounds having a

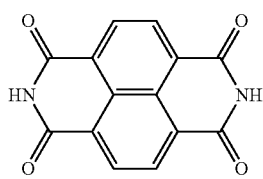 [SMILES: O=C1NC(=O)c2ccc3c4c(ccc1c24)C(=O)NC3=O]

backbone structure according to the present invention have antibiotic activity, especially antibiotic activity against Gram positive bacteria. It is further surprising, that some of the compounds tested do have activity against *Staphylococcus aureus*. This especially applies to the subset of compounds that are asymmetrical (as defined below).

The invention accordingly relates to an antibiotic compound, having the formula I

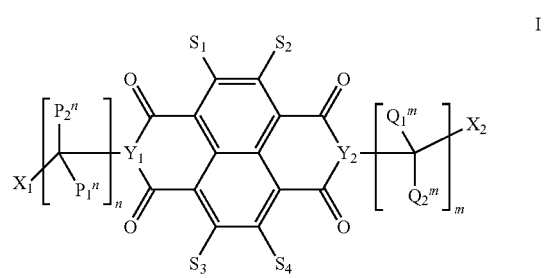

wherein $S_1$, $S_2$, $S_3$, $S_4$ are independently H, F, Cl, Br, I, hydroxy-, thiol-, thioether, $NH_2$, nitro-, cyano-, isocyano-, carboxylic acid, alkyl-, hydroxyalkyl-, alkoxy-alkoxyalkyl-, a carbocyclic- or a heterocyclic group, or

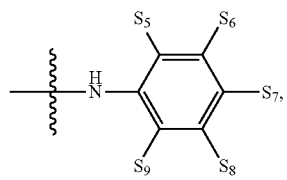

wherein $S_5$-$S_9$ is independently H or F;

wherein $Y_1$ and $Y_2$ are selected from the group of CH, CF, C-alkyl, C-alkoxy, C-alkoxyalkyl, C-carbocycle, C-heterocycle or N, preferably wherein at least one of $Y_1$ and $Y_2$=N, and the other of $Y_1$ and $Y_2$ is CH, CF, C-alkyl, C-alkoxy, C-alkoxyalkyl, C-carbocycle, C-heterocycle or N, more preferably wherein $Y_2$ is N, CH, CF or C-alkyl;

n, m are independently 0-8;

$P''_1$, $P''_2$, $Q'''_1$, $Q'''_2$ are independently H, halogen, alkyl, alkoxy, alkoxyalkyl, carbocycle or heterocycle;

wherein if n=0 or 1, then $X_1$ is H, $OX_3$,

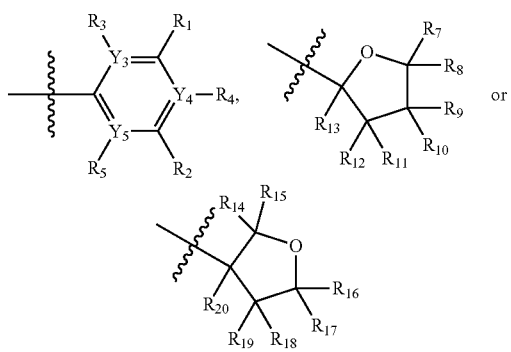

wherein if m=0 or 1, then $X_2$ is H, $OX_3$,

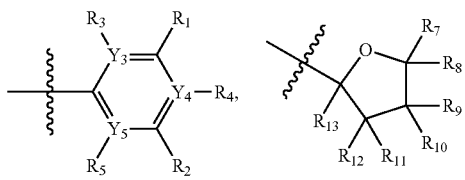

and
and wherein if n=2-8, then $X_1$=$OX_3$,

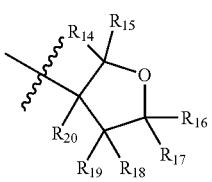 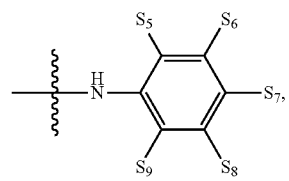

and wherein if m=2-8, then $X_2$=$OX_3$,

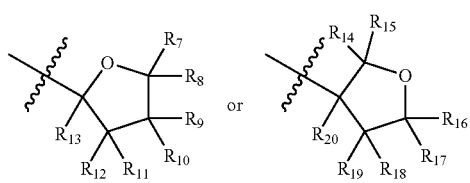

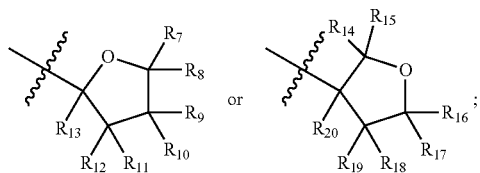

wherein one of $Y_3$, $Y_4$ and $Y_5$ is C or N, and the others of $Y_3$, $Y_4$ and $Y_5$ are C, and that if $Y_n$=N, the R-group on that N-atom is void;

wherein $R_1$-$R_5$ are independently H, OH, alkyl, alkoxy, alkoxyalkyl, carbocycle or heterocycle, preferably OMe, C(O)CH$_3$ or C(O)—OCH$_3$; wherein $X_3$=H, alkyl or (—CO)—$R_6$, wherein $R_6$=alkyl;

and wherein $R_7$-$R_{20}$ are independently H, F, Cl, Br, I, hydroxy-, thiol-, thioether, NH$_2$, nitro-, cyano-, isocyano-, carboxylic acid, alkyl-, hydroxyalkyl-, alkoxy-, alkoxyalkyl-, a carbocyclic- or a heterocyclic group; or a pharmaceutically available salt thereof.

Preferably in compounds of formula I, $Y_1$=$Y_2$=N. Further preferred compounds are compounds in which when one of $X_1$ and $X_2$ is H the other of $X_1$ and $X_2$ is not H. Also preferred are compounds in which $X_1$ is identical to $X_2$. Further preferred are compounds in which n=m, $Q_1$=$P_1$, $Q_2$=$P_2$ and $X_1$=$X_2$, which are called symmetrical compounds of formula I. Alternatively, also asymmetric compounds are included in the invention as have been exemplified in the experimental section.

Another category of compounds is formed by those compounds according to Formula I, wherein one, two, three or four of $S_1$, $S_2$, $S_3$, $S_4$ are independently

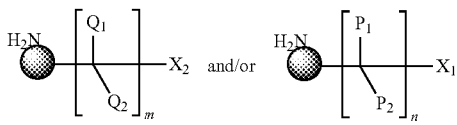

wherein $S_5$—$S_9$ is independently H or F.

Preferably in these compounds only one of $S_1$, $S_2$, $S_3$, $S_4$ is

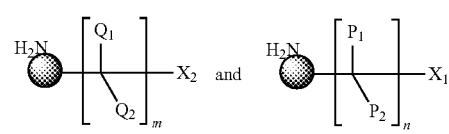

wherein $S_5$—$S_9$ is independently H or F, and the others of $S_1$, $S_2$, $S_3$, $S_4$ are H.

Compounds of Formula I in which $Y_1$=$Y_2$=N may be prepared by reacting a napthalene tetracarboxylic dianhydride with compounds in a condensation reaction, preferably in a polar solvent, wherein $S_1$, $S_2$, $S_3$, $S_4$, $Q_1$, $Q_2$, $P_1$, $P_2$, $X_1$, $X_2$ and n and m have the same meaning as indicated above.

In case of symmetrical naphthalene diimides, wherein n=m, $Q_1$=$P_1$, $Q_2$=$P_2$ and $X_1$=$X_2$, compounds are equal and reacted with a napthalene tetracarboxylic dianhydride as defined above. In case of asymmetrical naphthalene diimide, reaction with compounds

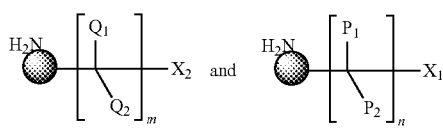

is preferably achieved in a multistep sequence, i.e. by first hydrolyzing one of the anhydrides of the napthalene tetracarboxylic dianhydride, then forming the first imide with one of the compounds

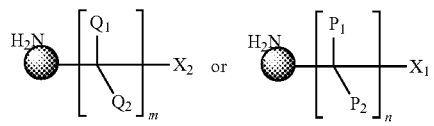

in a condensation reaction, then reforming the anhydride and finally forming the second imide by condensation with the second compound of

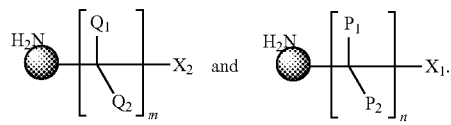

All these steps are well-known in the art.

Compounds of general formula I in which one of $Y_1$ and $Y_2$ is N, and in which the other of $Y_1$ and $Y_2$ is CH, CF, C-alkyl, C-alkoxy, C-alkoxyalkyl, C-carbocycle or C-heterocycle can be prepared by condensation of an appropriately substituted anhydride of structure

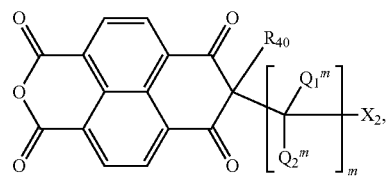

wherein $R_{40}$ is H, F, alkyl, alkoxy, alkoxyalkyl, carbocycle or heterocycle, with a compound of formula

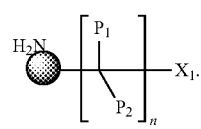

Preferably, compounds of formula I are selected from the following Table I:

TABLE I

Preferred compounds of the structural formula I.

Structure

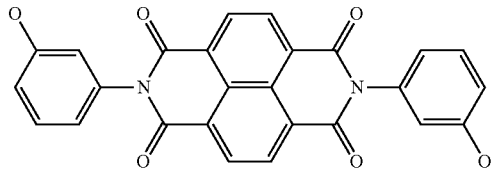 [SMILES: O=C1c2ccc3c4c(ccc(c24)C(=O)N1c1cccc(O)c1)C(=O)N(c1cccc(O)c1)C3=O]

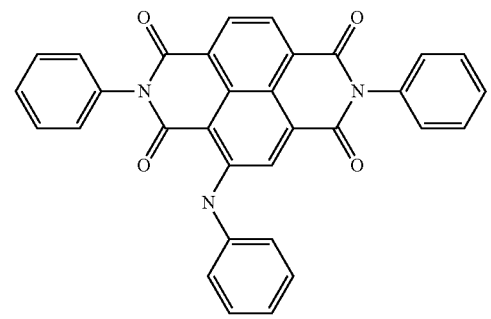 [SMILES: O=C1c2ccc3c4c(c(Nc5ccccc5)cc(c24)C(=O)N1c1ccccc1)C(=O)N(c1ccccc1)C3=O]

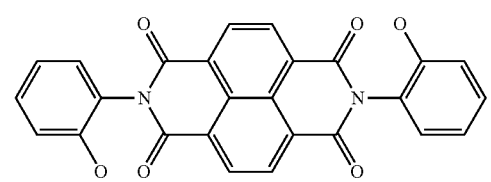 [SMILES: O=C1c2ccc3c4c(ccc(c24)C(=O)N1c1ccccc1O)C(=O)N(c1ccccc1O)C3=O]

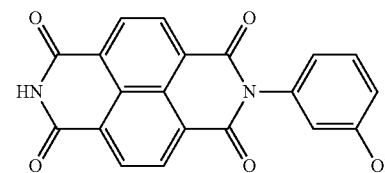

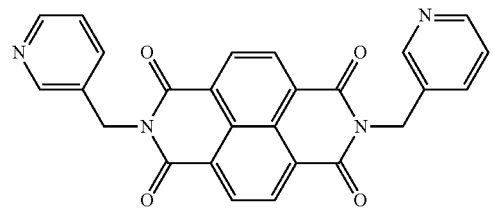 [SMILES: O=C1c2ccc3c4c(ccc(c24)C(=O)N1Cc1cccnc1)C(=O)N(Cc1cccnc1)C3=O]

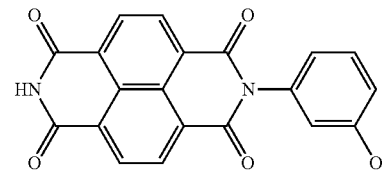 [SMILES: O=C1NC(=O)c2ccc3c4c(ccc1c24)C(=O)N(c1cccc(O)c1)C3=O]

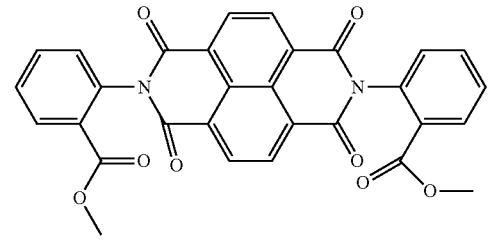 [SMILES: COC(=O)c1ccccc1N1C(=O)c2ccc3c4c(ccc(c24)C1=O)C(=O)N(c1ccccc1C(=O)OC)C3=O]

TABLE I-continued

Preferred compounds of the structural formula I.

Structure

TABLE I-continued

Preferred compounds of the structural formula I.

Structure

TABLE I-continued

Preferred compounds of the structural formula I.

Structure

[Chemical structures]

Most preferably, the compounds of formulae I are used as antimicrobial agents, in particular for the treatment of infections with Gram positive bacteria, such as *Bacillus, Clostridium* and *Staphylococcus* species, in particular for the treatment of infections with *Clostridium difficile*.

Compounds of formula I can be used in pharmaceutical compositions for the treatment of bacterial diseases, especially those diseases caused by Gram-positive bacteria such as *Bacillus, Clostridium* and *Staphylococcus* species, especially *Clostridium* and more specifically *C. difficile*, or in conditions wherein the subject runs the risk of being infected with said micro-organism(s).

The compounds of the invention or compositions therewith can, however, also be used in other than pharmaceutical applications, e.g. in cosmetics (e.g. for the treatment of acne), in detergents and/or other cleaning solutions, in anti-fouling paints, in food or feed or in food or feed packaging, and so on.

A compound according to the present invention, or a pharmaceutically acceptable salt or prodrug thereof, may be provided to a subject in need thereof for prophylactic or therapeutic reasons. A compound according to the present invention, or a pharmaceutically acceptable salt or prodrug thereof, may be provided to a subject in need thereof in the form of any pharmaceutical preparation, when such administration form is capable of treating and/or preventing infection in a subject. As a consequence of the prevention or treatment of infection, also the clinical effects or sequellae of infection will be prevented.

The present invention also relates to a method for preventing and/or treating infection in a subject, preferably a human or other mammalian subject, said method comprising administering to said subject a therapeutically and/or prophylactically effective amount of a pharmaceutical composition comprising a compound according to the invention, o r pharmaceutically acceptable salts or prodrugs thereof and a pharmaceutically acceptable carrier, and optionally one or more excipients.

The present invention also relates to the use of a compound according to the invention, or pharmaceutically acceptable salts or prodrugs thereof for the manufacture of a medicament for treating bacterial infection, preferably infection with Gram-positive bacteria, most preferably *Clostridium* infection.

An antibiotic therapy (i.e. the method for preventing and/or treating infection in a subject) may also comprise administering to an otherwise healthy individual, at risk of developing infection, a prophylactically effective amount of the pharmaceutical composition.

Dosages for achieving the antibiotic effects of the pharmaceutical composition described herein may easily be determined by the skilled person. For purposes of the present invention, an effective dose will be a daily dose between about 0.01 mg and 10 grams of the compound according to the invention for an adult human being. More preferably a dose between 0.1 mg and 1 gram is used, even more preferably a dose of 1 mg-100 mg and most preferably a dose of 4-40 mg of the compound of the invention is administered. This daily dose may be given as a one-dose administration, or it may be subdivided in several subdoses, which are administered spread over the day.

For oral administration, the compositions may be packed in e.g. gelatin capsules or may be tableted in the form of tablets or may be given in liquid compositions. For oral therapeutic application the active compound may be administered with excipients and e.g. used in the form of powders, sachets, tablets, pills, pastilles or capsules. The pharmaceutical compositions may be prepared by conventional means with pharmaceutically acceptable excipients such as binding agents (e.g. pregelatinised maize starch, tragacanth gum, gelatine, polyvinylpyrrolidone or hydroxypropyl methylcellulose); fillers (e.g. lactose, microcrystalline cellulose, mannitol or calcium hydrogen phosphate); lubricants (e.g. magnesium stearate, talc or silica); disintegrants (e.g. potato starch, sodium starch glycollate or alginate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For buccal administration the compositions may take the form of tablets or lozenges formulated in conventional manner.

The compounds according to the present invention may be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g. sterile pyrogen-free water, before use.

When dosing is in the form of a capsule, the capsule may comprise apart from the elements mentioned above a liquid carrier such as an oil. Dosage form may further be provided with coatings of sugar, shellac or other agents. The components of the pharmaceutical composition are preferably chosen such that they do not reduce the desired working of the active compound.

The pharmaceutical compositions can further comprise flavoring sweetening, coloring and/or preservative agents.

A compound according to the invention, or a pharmaceutically acceptable salt or prodrug thereof may also be administered in the form of e.g. an elixir, a suspension, a syrup, a waffle or a chewing gum.

In a pharmaceutical composition as described above, a compound or a pharmaceutically acceptable salt or prodrug thereof, is used in an amount of from 0.01 to 99.9% by weight, preferably from 0.01 to 10 wt. %, and more preferably from 0.05 to 5 wt. %.

The present invention further relates to a method for the preparation of a pharmaceutical composition for preventing and/or treating infection, comprising processing or incorporating a compound according to the invention, or a pharmaceutically acceptable salt or prodrug thereof, as an active substance, together with a pharmaceutically acceptable carrier in a pharmaceutical composition.

The preparation of a pharmaceutical composition may very suitably occur by mixing all separate ingredients such as fillers, binders, lubricants and optionally other excipients together with a compound according to the invention, or a pharmaceutically acceptable salt or prodrug thereof, and processing the mixture obtained to a pharmaceutical preparation.

Further part of the invention is a combination composition or therapy with other antibiotic compounds in order to ensure a broad-spectrum effect. In such a broad-spectrum effect, the combination will be effective against *Clostridum*, but also against other bacteria. In order to obtain such a broad-spectrum effect especially preferred are antibiotics which work against Gram negative bacteria, such as beta-lactams, like penicillin, ampicillin, amoxycillin, oxacillin, carbenicillin and derivatives, ticarcillin, aziocillin, methycillin, mezocillin, and piperacillin, cephalosporins such as cephapirin, cefazolin, cephalexin, cefadroxil, cephradine, cefamandolenafate, cefonicid, cefuroxime, cefoxitim, cefotetan, cefaclor, cefprozil, loracarbacef, cefotaxime, ceftazidime, ceftozoxime, cefoperazone, ceftriaxone, cefixime, ceftibutem, cefdinir and cefpodoxime proxetil, carbapenems such as imipenem and miripinem, aminoglycosides such as gentamycin, amikacin and tobramycin, tazobactam, clindamycin, ciprofloxacin, sulbactam, aztrianam, chloramphenicol, colistin, nitrofurantoin, tetracycline, polymixin B, neomycin, trimethoprim and sulfamethoxazole. They may be combined into the same dosage form, or they may be applied as a combination therapy with either simultaneous or separate administration.

EXAMPLES

Example 1. Synthesis of N,N'-bis[(2-hydroxyethyl)]-1,4,6,8-naphthalene diimide

CAS Number: 53206-45-4
IUPAC Name: 2,7-BIS-(2-HYDROXY-ETHYL)-BENZO(LMN)(3,8)PHENANTHROLINE-1,3,6,8-TETRAONE The synthetic route for obtaining N,N'-bis[(2-hydroxyethyl)]-1,4,6,8-naphthalene diimide
is presented in Scheme 1.

N,N'-bis[(2-hydroxyethyl)]-1,4,6,8-naphthalene diimide was synthesized by condensation of 1,4,6,8-tetracarboxilic dianhydride (2.68 g, 0.01 mol) and 2-aminoethanol (1.9 ml, 0.04 mol) in aqueous solution. The suspension was heated at 80° C. for 8 h. The precipitate was filtered and washed with acetone.

N,N-bis[(2-hydroxyethyl)]-1,4,6,8-naphthalene diimide Yield (81%) m.p.=321-323° C.; FT-IR (KBr)cm$^{-1}$: 1704, 1660, 1337, 768; 1H NMR-(DMSO-d6): δ (ppm): 8.46 (s, 4H) 4.85 (t, 2H, OH); 4.10 (t, 2×HOCH$_2$); 3.63 (q, 4H, 2×CH$_2$N) 13C NMR-(DMSO-d6): 162.4 (2×C O), 130.3 (4C, CH), 125.9 (C-quat., 4C), 125.7 (Cquat., 2C), 57.6 (2×NCH$_2$), 42.2 (2×CH$_2$OH). Elemental analysis-C$_{18}$H$_{14}$N$_2$O$_6$ (354.1): calculated (%) C, 61.86, H, 3.95, N, 7.91; found (%) C, 61.79, H, 3.86, N, 7.83.

Scheme 1. Synthesis of N,N'-bis[(2-hydroxyethyl)]-1,4,6,8-naphthalene diimide

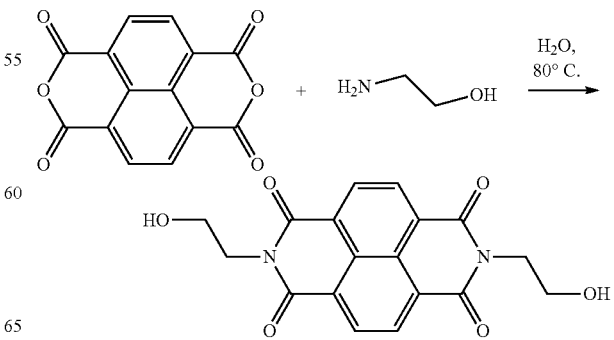

Example 2. Synthesis of naphthalene-1,8:4,5-tetracarboxydiimide

CAS Number: 5690-24-4
IUPAC Name: Naphthalene-1,8:4,5-tetracarboxydiimide
The synthetic route for obtaining Naphthalene-1,8:4,5-tetracarboxydiimide is presented in Scheme 2.

Preparation of 1,4,5,8-naphthalenetetracarboxylic diimide 1,4,5,8-naphthalenetetracarboxylic dianhidride (12.5 g, 46.6 mmol) was dissolved in a stirred concentrated aqueous solution of ammonium hydroxide (625 mL, 29.5%, w/w).

The reaction mixture was stirred at room temperature under nitrogen. During that time, analytically pure 1,4,5,8-naphthalenetetracarboxylic diimide precipitated as a pale yellow product, which was filtered, washed with distilled water, and dried under vacuum at 60° overnight. Yield: 11.9 g (96%); mp>350; H nmr (400 MHz, $D_2SO_4$): δ 165.5, 134.9, 127.8, 125.4.

Elemental analysis for $C_{14}H_{60}O_4N_2$ (354.1): calculated (%) C, 63.17, H, 2.27, N, 10.52; found (%) C, 62.98, H, 2.28, N, 10.48.

Scheme 2. Synthesis of Naphthalene-1,8:4,5-tetracarboxydiimide.

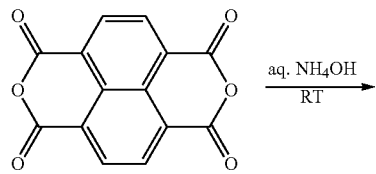
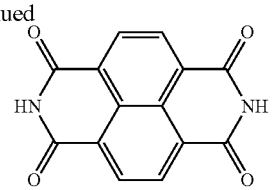

Example 3. MIC Tests with Symmetrical Compounds

Growth inhibition experiments were performed according to the following protocol:

*C. difficile* spores (ATCC 43599) were diluted 10000× times in distilled water from a stock solution ($10^9$ per ml) in SAB medium pH7.3 (Oxoid CM0497) containing 0.1% sodium taurocholate. Microtiter plate wells were filled with 495 microliter of this suspension to which 5 microliter of selected compounds dissolved in DMSO was added (final concentration of each compound was 10 microgram per ml). This was all performed in an anaerobic cabinet. After filling the microtiter plate was sealed and incubated for 22 hours at 37° C. Inhibiting compounds were selected by visually determining growth inhibition.

Tests with *C. perfringens* were performed on *C. perfringens* vegetative cells from strain ATCC 13124. The protocol was as described above.

The compounds in Table 2 showed an MIC of less than 10 microgram/ml dose per microtiter well.

TABLE 2

List of compounds that showed an MIC of <10 μg/ml aginst *C. perfringens* or *C. difficile*.

| Structure | Molecular Weight | Formula |
|---|---|---|
| 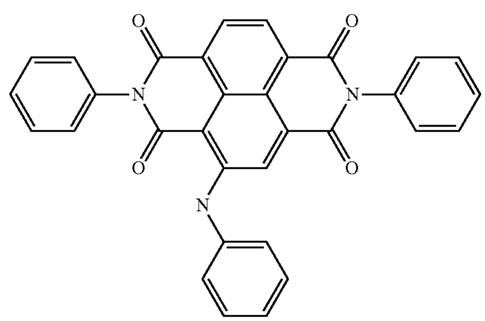 [SMILES: O=C1c2ccc3c4c(c(Nc5ccccc5)cc(c24)C(=O)N1c1ccccc1)C(=O)N(c1ccccc1)C3=O] | 509.51 | C32H19N3O4 |
| | 450.40 | C26H14N2O6 |
| | 450.40 | C26H14N2O6 |

TABLE 2-continued

List of compounds that showed an MIC of <10 μg/ml aginst *C. perfringens* or *C. difficile*.

| Structure | Molecular Weight | Formula |
|---|---|---|
| 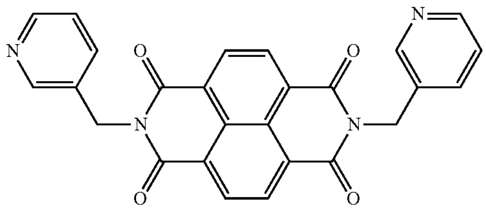 [SMILES: O=C1c2ccc3c4c(ccc(c24)C(=O)N1Cc1cccnc1)C(=O)N(Cc1cccnc1)C3=O]  | 448.43 | C26H16N4O4 |
| 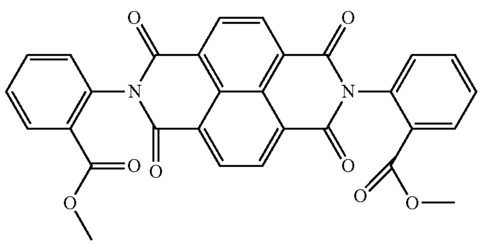 [SMILES: COC(=O)c1ccccc1N1C(=O)c2ccc3c4c(ccc(c24)C1=O)C(=O)N(c1ccccc1C(=O)OC)C3=O]  | 534.47 | C30H18N2O8 |
| 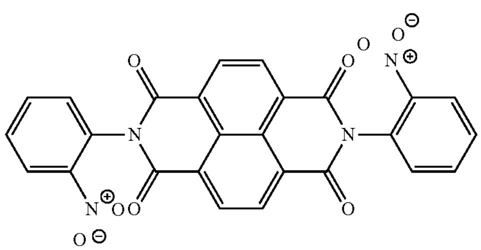  | 508.40 | C26H12N4O8 |
| 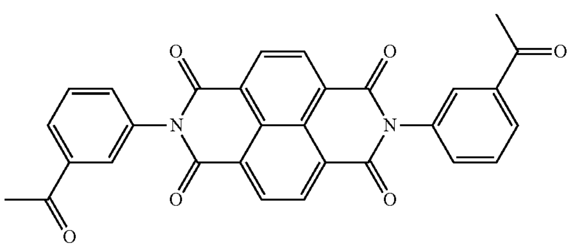 [SMILES: CC(=O)c1cccc(N2C(=O)c3ccc4c5c(ccc(c35)C2=O)C(=O)N(c2cccc(C(C)=O)c2)C4=O)c1]  | 502.47 | C30H18N2O6 |
| 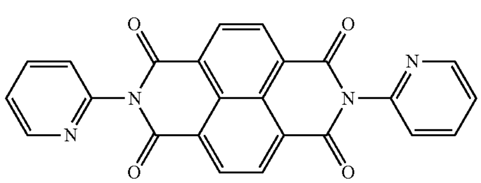 [SMILES: O=C1c2ccc3c4c(ccc(c24)C(=O)N1c1ccccn1)C(=O)N(c1ccccn1)C3=O]  | 420.38 | C24H12N4O4 |
| 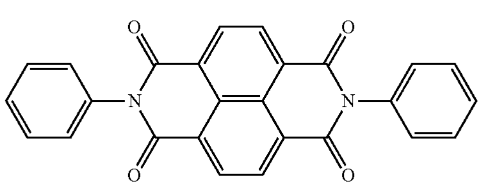 [SMILES: O=C1c2ccc3c4c(ccc(c24)C(=O)N1c1ccccc1)C(=O)N(c1ccccc1)C3=O]  | 418.40 | C26H14N2O4 |
| 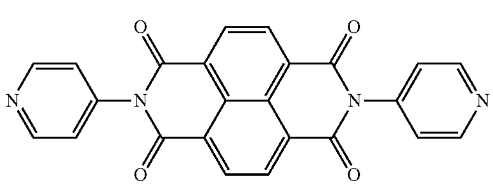 [SMILES: O=C1c2ccc3c4c(ccc(c24)C(=O)N1c1ccncc1)C(=O)N(c1ccncc1)C3=O]  | 420.38 | C24H12N4O4 |

TABLE 2-continued

List of compounds that showed an MIC of <10 µg/ml aginst *C. perfringens* or *C. difficile*.

| Structure | Molecular Weight | Formula |
|---|---|---|
| 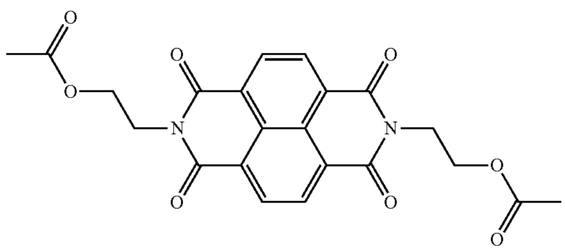 [SMILES: CC(=O)OCCN1C(=O)c2ccc3c4c(ccc(c24)C1=O)C(=O)N(CCOC(C)=O)C3=O] | 438.39 | C22H18N2O8 |
| 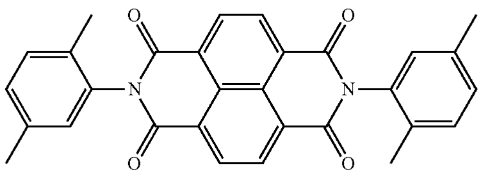 [SMILES: Cc1ccc(C)c(N2C(=O)c3ccc4c5c(ccc(c35)C2=O)C(=O)N(c2cc(C)ccc2C)C4=O)c1] | 474.51 | C30H22N2O4 |
| 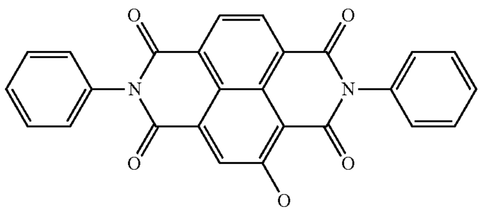 [SMILES: O=C1c2ccc3c4c(c(O)cc(c24)C(=O)N1c1ccccc1)C(=O)N(c1ccccc1)C3=O] | 452.85 | C26H13ClN2O4 |
| 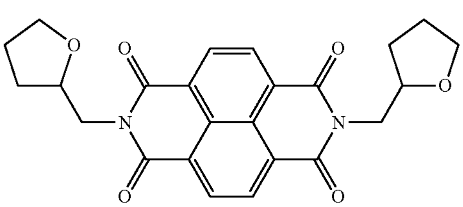 [SMILES: O=C1c2ccc3c4c(ccc(c24)C(=O)N1CC1CCCO1)C(=O)N(CC1CCCO1)C3=O] | 434.44 | C24H22N2O6 |
| 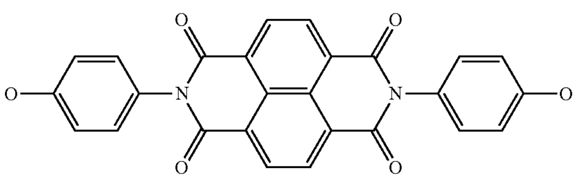 [SMILES: O=C1c2ccc3c4c(ccc(c24)C(=O)N1c1ccc(O)cc1)C(=O)N(c1ccc(O)cc1)C3=O] | 450.40 | C26H14N2O6 |
| 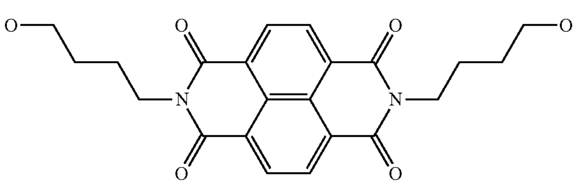 [SMILES: O=C1c2ccc3c4c(ccc(c24)C(=O)N1CCCCO)C(=O)N(CCCCO)C3=O] | 410.42 | C22H22N2O6 |
| 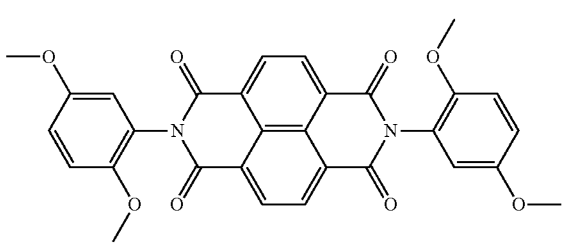 | 538.50 | C30H22N2O8 |

TABLE 2-continued

List of compounds that showed an MIC of <10 µg/ml aginst *C. perfringens* or *C. difficile*.

| Structure | Molecular Weight | Formula |
|---|---|---|
| 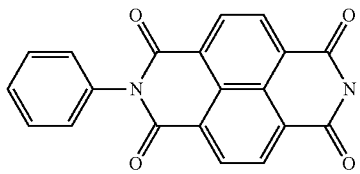 [SMILES: O=C1NC(=O)c2ccc3c4c(ccc1c24)C(=O)N(c1ccccc1)C3=O] | 342.30 | C20H10N2O4 |
| 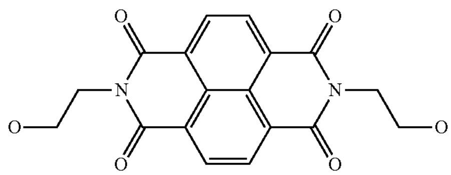 [SMILES: O=C1c2ccc3c4c(ccc(c24)C(=O)N1CCO)C(=O)N(CCO)C3=O] | 354.32 | C18H14N2O6 |
| 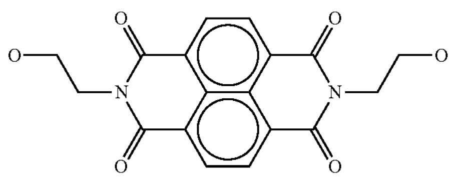 | 354.31 | C18H14N2O6 |
| 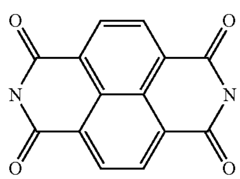 [SMILES: O=C1NC(=O)c2ccc3c4c(ccc1c24)C(=O)NC3=O] | 266.21 | C14H6N2O4 |

Example 4. MIC Tests with Asymmetrical Compounds

According to the same protocol as in Example 3 asymmetrical compounds were tested on their inhibitory effect of *C. difficile*, but also on other bacterial species, such as *S. aureus* and *B. cereus*.

In the below tables the compounds and the MIC values that have been found for the various micro-organisms are listed. In the tests described in Table 4 and 5 the medium indicated as 'flora' is the SIEM medium described in Ladirat S E, Schols H A, Nauta A, Schoterman M H, Keijser B J, Montijn R C, Gruppen H, Schuren F H. High-throughput analysis of the impact of antibiotics on the human intestinal microbiota composition. J Microbiol Methods. 2013 March; 92(3):387-97.

TABLE 3

Asymmetric compounds and their MIC values obtained from an experiment on vegetative cells and spores of *C. difficile* ATCC 43599. If not indicated otherwise, tested concentrations were from 10 µg/ml-0.003 µg/ml.

| compound | structure | MIC (ug/ml) Veg. cells | MIC (ug/ml) spores |
|---|---|---|---|
| 20141155PBmol08 | 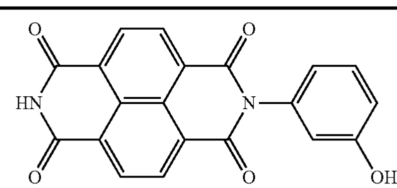 | 0.07-0.15 | 0.03-0.07 |
| 20141155PBmol10 | 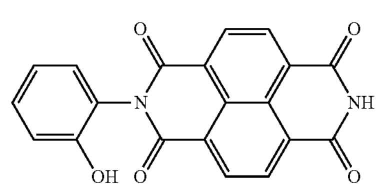 [SMILES: O=C1NC(=O)c2ccc3c4c(ccc1c24)C(=O)N(c1ccccc1O)C3=O] | 0.3-0.6 | 0.15-0.3 |

TABLE 3-continued

Asymmetric compounds and their MIC values obtained from an experiment on vegetative cells and spores of *C. difficile* ATCC 43599. If not indicated otherwise, tested concentrations were from 10 μg/ml-0.003 μg/ml.

| compound | structure | MIC (ug/ml) Veg. cells | MIC (ug/ml) spores |
| --- | --- | --- | --- |
| 20141155PBmol16 | 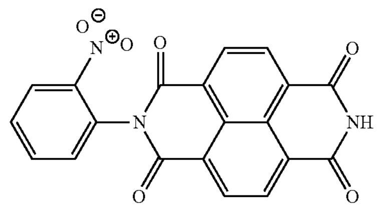 | 0.03-0.07 | 0.01-0.03 |
| 20141155PBmol17 | 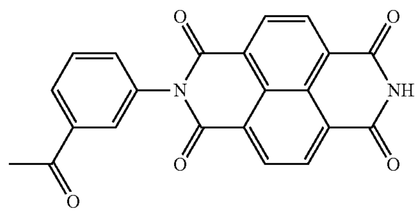 [SMILES: CC(=O)c1cccc(N2C(=O)c3ccc4c5c(ccc(c35)C2=O)C(=O)NC4=O)c1] | 0.01-0.03 | 0.01-0.03 |
| 20141155PBmol18 | 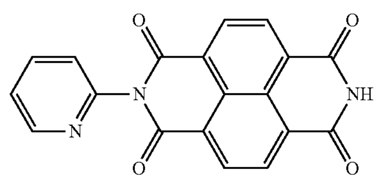 [SMILES: O=C1NC(=O)c2ccc3c4c(ccc1c24)C(=O)N(c1ccccn1)C3=O] | 0.07-0.15 | 0.07-0.15 |
| 20141155PBmol19 | 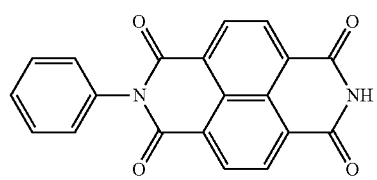 [SMILES: O=C1NC(=O)c2ccc3c4c(ccc1c24)C(=O)N(c1ccccc1)C3=O] | 0.01-0.03 | 0.007-0.01 |
| 20141155PBmol21 | 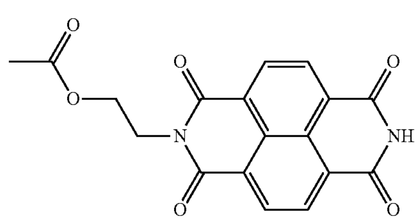 [SMILES: CC(=O)OCCN1C(=O)c2ccc3c4c(ccc(c24)C1=O)C(=O)NC3=O] | 0.03-0.07 | 0.01-0.03 |
| 20141155PBmol23 | 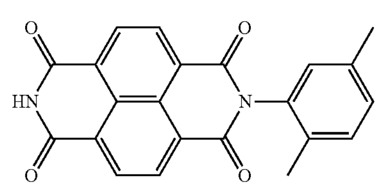 [SMILES: Cc1ccc(C)c(N2C(=O)c3ccc4c5c(ccc(c35)C2=O)C(=O)NC4=O)c1] | 0.07-0.15 | 0.03-0.07 |
| 20141155PBmol30 | 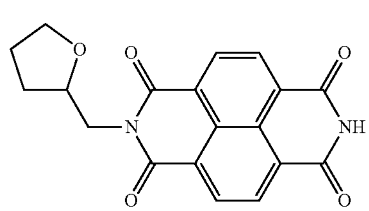 [SMILES: O=C1NC(=O)c2ccc3c4c(ccc1c24)C(=O)N(CC1CCCO1)C3=O] | 0.03-0.07 | 0.01-0.03 |

TABLE 3-continued

Asymmetric compounds and their MIC values obtained from an experiment on vegetative cells and spores of *C. difficile* ATCC 43599. If not indicated otherwise, tested concentrations were from 10 μg/ml-0.003 μg/ml.

| compound | structure | MIC (ug/ml) Veg. cells | MIC (ug/ml) spores |
| --- | --- | --- | --- |
| 20141155PBmol37 | 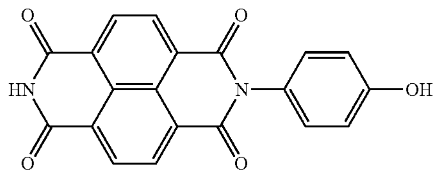 [SMILES: O=C1NC(=O)c2ccc3c4c(ccc1c24)C(=O)N(c1ccc(O)cc1)C3=O] | 0.07-0.15 | 0.03-0.07 |
| 20141155PBmol41 | 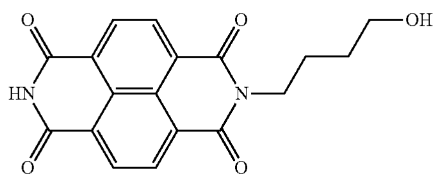 [SMILES: O=C1NC(=O)c2ccc3c4c(ccc1c24)C(=O)N(CCCCO)C3=O] | 0.07-0.15 | 0.03-0.07 |
| 20141155PBmol46 | 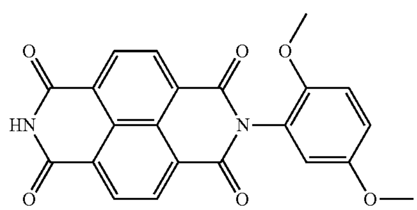 [SMILES: COc1ccc(OC)c(N2C(=O)c3ccc4c5c(ccc(c35)C2=O)C(=O)NC4=O)c1] | 0.07-0.15 | 0.03-0.07 |
| 20141155PBmol57 | 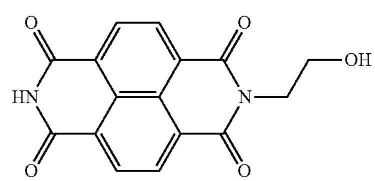 | 0.15-0.3 | 0.15-0.3 |
| A0547/0025269 * | 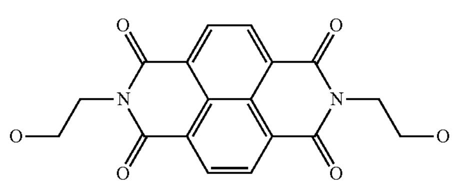 [SMILES: O=C1c2ccc3c4c(ccc(c24)C(=O)N1CCO)C(=O)N(CCO)C3=O] | 0.3-0.6 | 0.3-0.6 |
| 4456-3445 (6739753) | 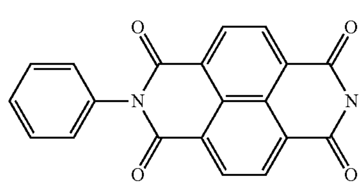 [SMILES: O=C1NC(=O)c2ccc3c4c(ccc1c24)C(=O)N(c1ccccc1)C3=O] | <0.3* | <0.3* |
| Vancomycin | | <0.3* | <0.3* |
| Metronadizol | | <0.3* | <0.3* |

*No higher dose tested

TABLE 4

Asymmetric compounds and their MIC values obtained from an experiment on vegetative cells and spores of *C. difficile* ATCC 43599. If not indicated otherwise, tested concentrations were from 1.2 μg/ml-0.03 μg/ml

| compound | structure | veg. cells | spores | veg. cells | spores |
|---|---|---|---|---|---|
| | | MIC (ug/ml) | | | |
| | | SAB model medium | | flora | |
| 20141155PBmol08 | | 0.15-0.3 | 0.07-0.15 | 0.6-1.2 | 0.6-1.2 |
| 20141155PBmol10 | | 0.3-0.6 | 0.3-0.6 | 0.15-0.3 | >1.2 |
| 20141155PBmol16 | | 0.07-0.15 | 0.07-0.15 | 0.6-1.2 | >1.2 |
| 20141155PBmol17 | | 0.03-0.07 | 0.03-0.07 | 0.3-0.6 | >1.2 |
| 20141155PBmol18 | | 0.07-0.15 | 0.07-0.15 | 0.15-0.3 | 0.3-0.6 |
| 20141155PBmol19 | | <0.03 | <0.03 | 0.15-0.3 | 0.15-0.03 |
| 20141155PBmol21 | | 0.03-0 07 | 0.03-0.07 | 0.15-0.3 | 0.3-0.6 |

TABLE 4-continued

Asymmetric compounds and their MIC values obtained from an experiment on vegetative cells and spores of *C. difficile* ATCC 43599. If not indicated otherwise, tested concentrations were from 1.2 μg/ml-0.03 μg/ml

| compound | structure | veg. cells | spores | veg. cells | spores |
|---|---|---|---|---|---|
| | | MIC (ug/ml) | | | |
| | | SAB model medium | | flora | |
| 20141155PBmol23 | | 0.07-0.15 | 0.07-0.15 | 0.3-0.6 | >1.2 |
| 20141155PBmol30 | | 0.03-0.07 | 0.03-0.07 | 0.3-0.6 | 0.3-0.6 |
| 20141155PBmol37 | | 0.07-0.15 | 0.07-0.15 | 0.6-1.2 | 0.3-0.6 |
| 20141155PBmol41 | | 0.07-0.15 | 0.07-0.15 | 0.15-0.3 | 0.15-0.3 |
| 20141155PBmol46 | | 0.07-0.15 | 0.07-0.15 | 0.6-1.2 | 0.6-1.2 |
| 20141155PBmol57 | | 0.3-0.6 | 0.3-0.6 | 0.07-0.15 | 0.6-1.2 |
| A0547/0025269 * | | 0.6-1.2 | 0.3-0.6 | 0.3-0.6 | 0.6-1.2 |

TABLE 4-continued

Asymmetric compounds and their MIC values obtained from an experiment on vegetative cells and spores of *C. difficile* ATCC 43599. If not indicated otherwise, tested concentrations were from 1.2 µg/ml-0.03 µg/ml

| compound | structure | veg. cells | spores | veg. cells | spores |
|---|---|---|---|---|---|
| | | MIC (ug/ml) | | | |
| | | SAB model medium | | flora | |
| 4456-3445 (6739753) * | [structure] | <0.3 | <0.3 | 0.6-1.2 | 0.6-1.2 |
| Vancomycin * | | <0.3 | <0.3 | <0.3 | <0.3 |
| Metronadizol * | | <0.3 | <0.3 | <0.3 | <0.3 |

* No higher dose tested

TABLE 5

Asymmetric compounds and their MIC values obtained from an experiment on *Staphylococcus aureus* and *Bacillus cereus*. MIC values in µg/ml.

| ID | Structure | MIC *S. aureus* ATCC 6538 | MIC *B. cereus* ATCC 11778 |
|---|---|---|---|
| 20141155PBmol08 | [structure] | >100 | 10 |
| 20141155PBmol21 | [structure] | >100 | 40 |
| 20141155PBmol10 | [structure] | 40 | 4 |
| 20141155PBmol23 | [structure] | >100 | 100 |
| 20141155PBmol13 | [structure] | >100 | >100 |

TABLE 5-continued

Asymmetric compounds and their MIC values obtained from an experiment on *Staphylococcus aureus* and *Bacillus cereus*. MIC values in µg/ml.

| ID | Structure | MIC *S. aureus* ATCC 6538 | MIC *B. cereus* ATCC 11778 |
|---|---|---|---|
| 20141155PBmol30 | 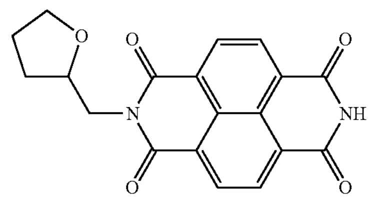 [SMILES: O=C1NC(=O)c2ccc3c4c(ccc1c24)C(=O)N(CC1CCCO1)C3=O] | >100 | >100 |
| 20141155PBmol16 | 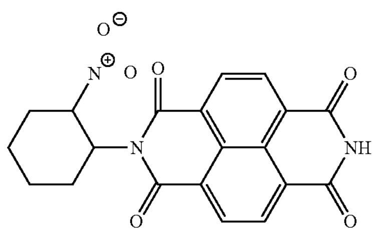 | 4 | 4 |
| 20141155PBmol37 | 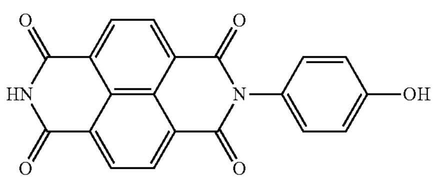 [SMILES: O=C1NC(=O)c2ccc3c4c(ccc1c24)C(=O)N(c1ccc(O)cc1)C3=O] | 40 | 4 |
| 20141155PBmol17 | 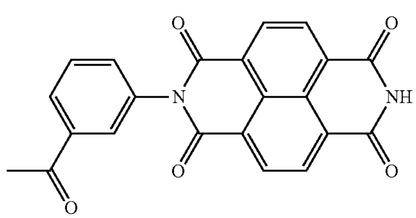 [SMILES: CC(=O)c1cccc(N2C(=O)c3ccc4c5c(ccc(c35)C2=O)C(=O)NC4=O)c1] | >100 | 4 |
| 20141155PBmol41 | 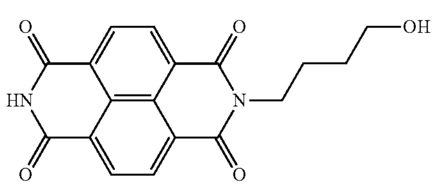 [SMILES: O=C1NC(=O)c2ccc3c4c(ccc1c24)C(=O)N(CCCCO)C3=O] | >100 | 4 |
| 20141155PBmol18 | 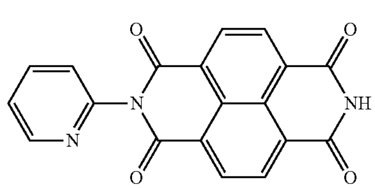 [SMILES: O=C1NC(=O)c2ccc3c4c(ccc1c24)C(=O)N(c1ccccn1)C3=O] | 40 | 4 |

TABLE 5-continued

Asymmetric compounds and their MIC values obtained from an experiment on *Staphylococcus aureus* and *Bacillus cereus*. MIC values in μg/ml.

| ID | Structure | MIC *S. aureus* ATCC 6538 | MIC *B. cereus* ATCC 11778 |
|---|---|---|---|
| 20141155PBmol46 | 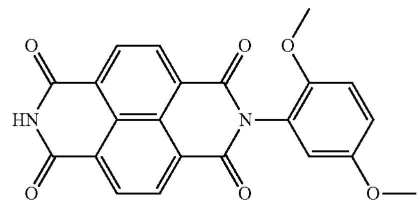 [SMILES: COc1ccc(OC)c(N2C(=O)c3ccc4c5c(ccc(c35)C2=O)C(=O)NC4=O)c1] | 10 | 4 |
| 20141155PBmol19 | 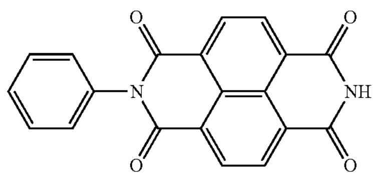 [SMILES: O=C1NC(=O)c2ccc3c4c(ccc1c24)C(=O)N(c1ccccc1)C3=O] | >100 | >100 |
| 20141155PBmol57 | 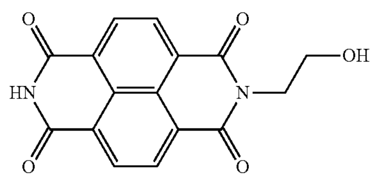 [SMILES: O=C1NC(=O)c2ccc3c4c(ccc1c24)C(=O)N(CCO)C3=O] | 40 | 4 |
| 20141155PBmol20 | 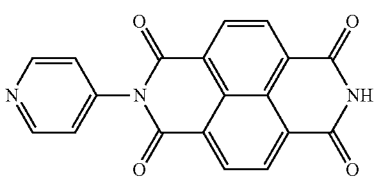 [SMILES: O=C1NC(=O)c2ccc3c4c(ccc1c24)C(=O)N(c1ccncc1)C3=O] | >100 | >100 |
| vanxcomycin | | 1 | 1 |

The invention claimed is:

1. A method to inhibit the growth of spore-forming Gram positive bacteria in a subject diagnosed as having an infection with spore-forming Gram positive bacteria said method comprising administering to said subject as the sole therapeutic agent one or more of the compounds of formula (I)

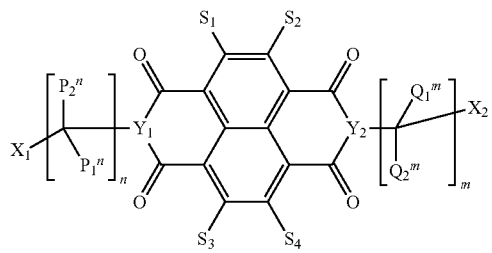

wherein
$S_1$, $S_2$, $S_3$, $S_4$ are independently H, F, Cl, Br, I, hydroxy-, thiol-, thioether, $NH_2$, nitro-, cyano-, isocyano-, carboxylic acid, alkyl-, hydroxyalkyl-, alkoxy-, alkoxyalkyl-, a carbocyclic- or a heterocyclic group, or

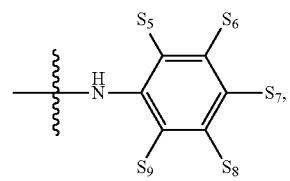

wherein $S_5$-$S_9$ is independently H or F;
wherein $Y_1$ and $Y_2$ are selected from the group consisting of CH, CF, C-alkyl, C-alkoxy, C-alkoxyalkyl, C-carbocycle, C-heterocycle or N;
n, m are independently 0-8;
$P''_1$, $P''_2$, $Q^m_1$, $Q^m_2$ are independently H, halogen, alkyl, alkoxy, alkoxyalkyl, carbocycle or heterocycle;
wherein if n=0 or 1, then $X_1$ is H, $OX_3$,

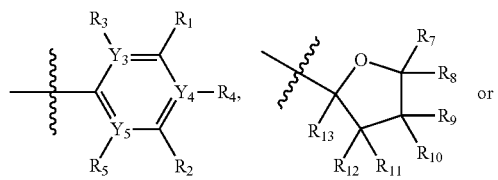

-continued

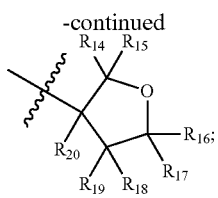

wherein if m=0 or 1, then $X_2$ is H, $OX_3$,

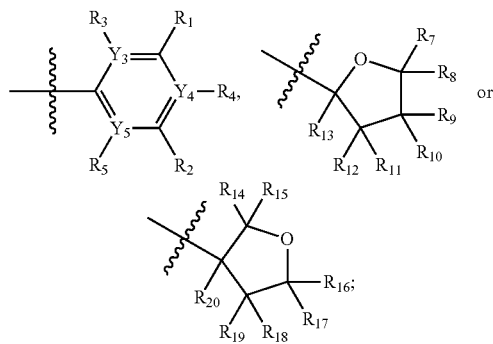

and
wherein if n is 2-8, then $X_1$=$OX_3$,

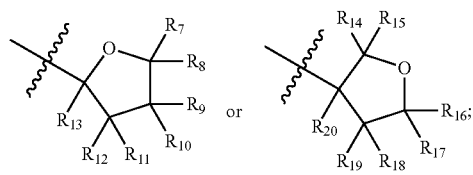

and
wherein if m=2-8, then $X_2$=$OX_3$,

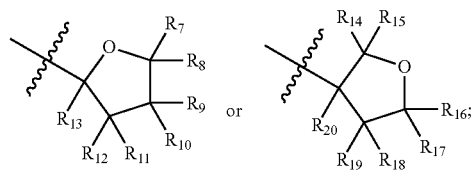

wherein one of $Y_3$, $Y_4$ and $Y_5$ is C or N, and the others of $Y_3$, $Y_4$ and $Y_5$ are C, and that if $Y_n$=N, the R-group on that N-atom is void;
wherein $R_1$-$R_5$ are independently H, OH, alkyl, alkoxy, alkoxyalkyl, carbocycle or heterocycle;
wherein $X_3$=H, alkyl or (—CO)—$R_6$, wherein $R_6$=alkyl; and
wherein $R_7$-$R_{20}$ are independently H, F, Cl, Br, I, hydroxy-, thiol-, thioether, $NH_2$, nitro-, cyano-, isocyano-, carboxylic acid, alkyl-, hydroxyalkyl-, alkoxy-, alkoxyalkyl-, a carbocyclic- or a heterocyclic group;
or a pharmaceutically acceptable salt thereof,
in an amount effective to inhibit the growth of said Gram-positive spore forming bacteria.

2. The method of claim 1, wherein $Y_1$=$Y_2$=N.
3. The method of claim 1, wherein one of $X_1$ and $X_2$ is H and the other of $X_1$ and $X_2$ is not H.
4. The method of claim 1, wherein $X_1$ is identical to $X_2$.
5. The method of claim 1, wherein one, two, three or four of $S_1$, $S_2$, $S_3$, $S_4$ are independently

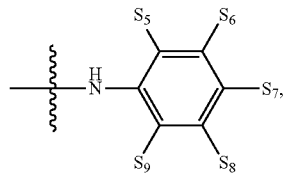

wherein $S_5$-$S_9$ is independently H or F.

6. The method of claim 5, wherein one of $S_1$, $S_2$, $S_3$, $S_4$ is

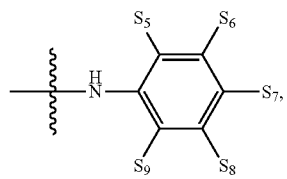

wherein $S_5$-$S_9$ is independently H or F and the others of $S_1$, $S_2$, $S_3$, $S_4$ are H.

7. The method of claim 3, wherein said compound is selected from the group consisting of:

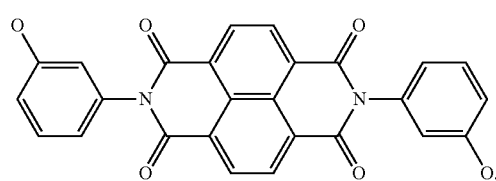

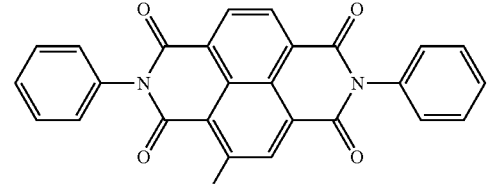

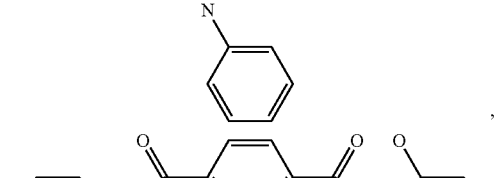

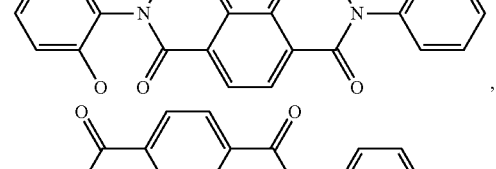

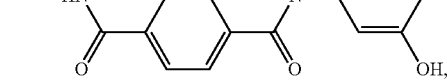

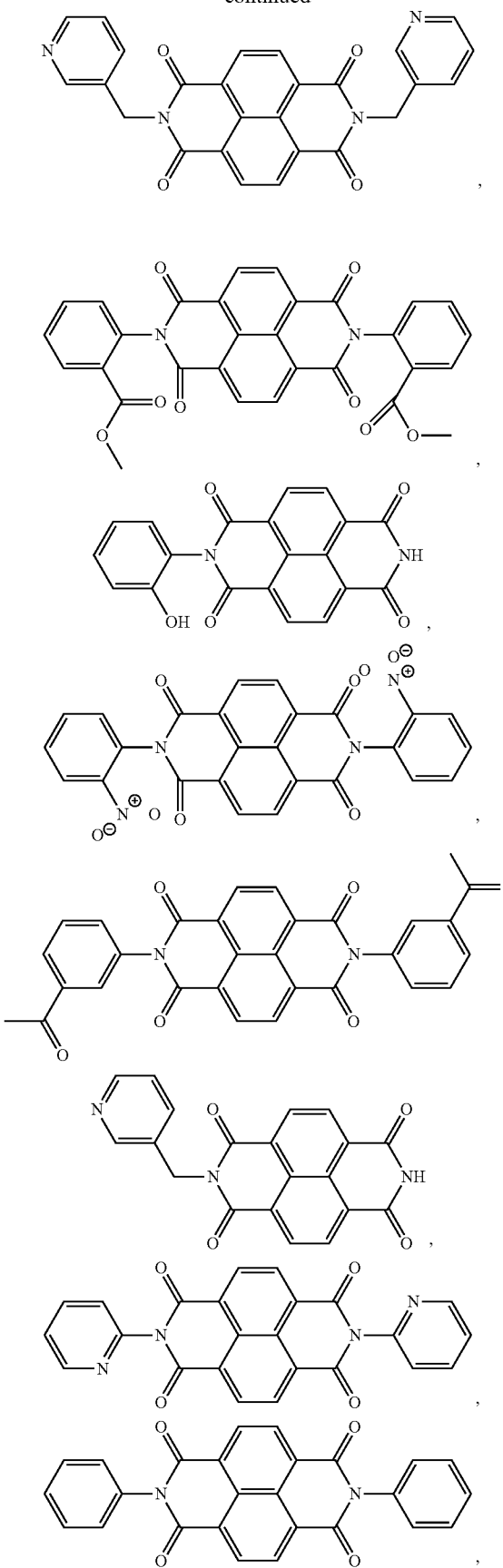
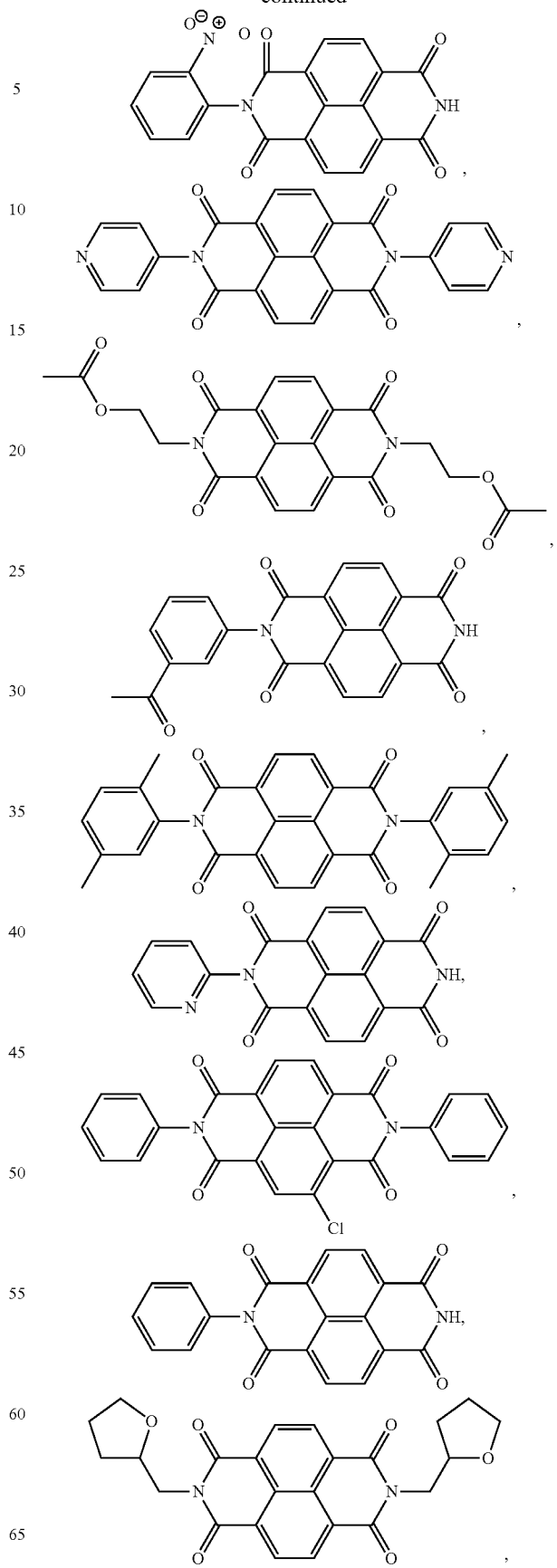

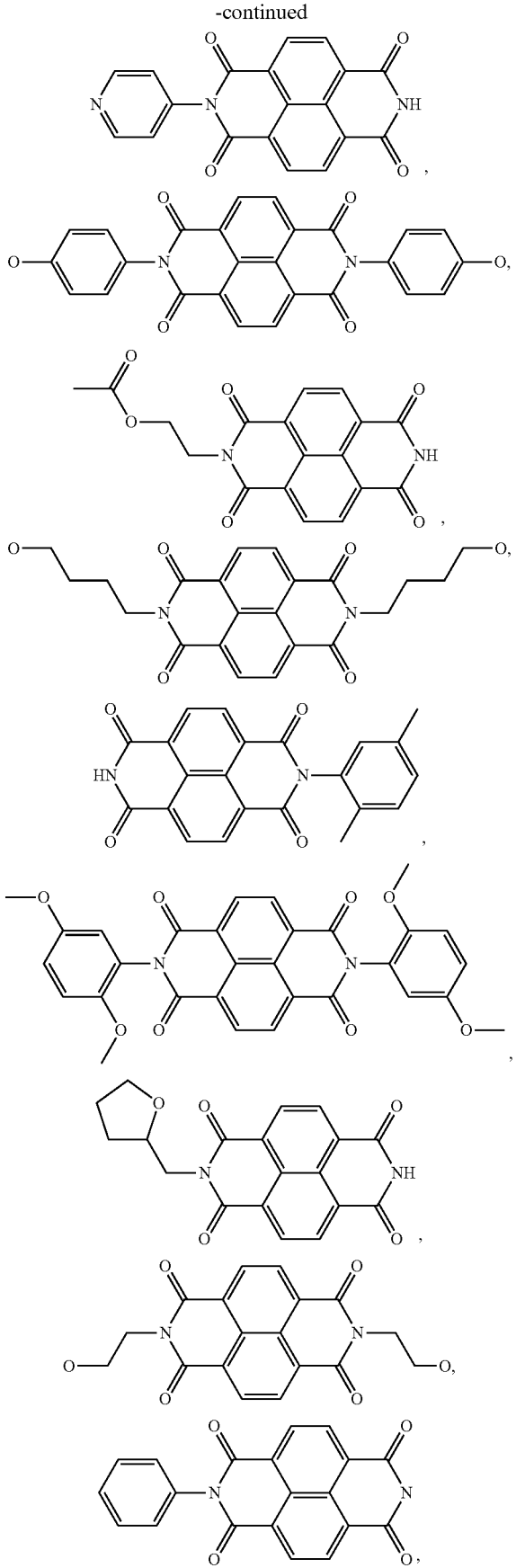
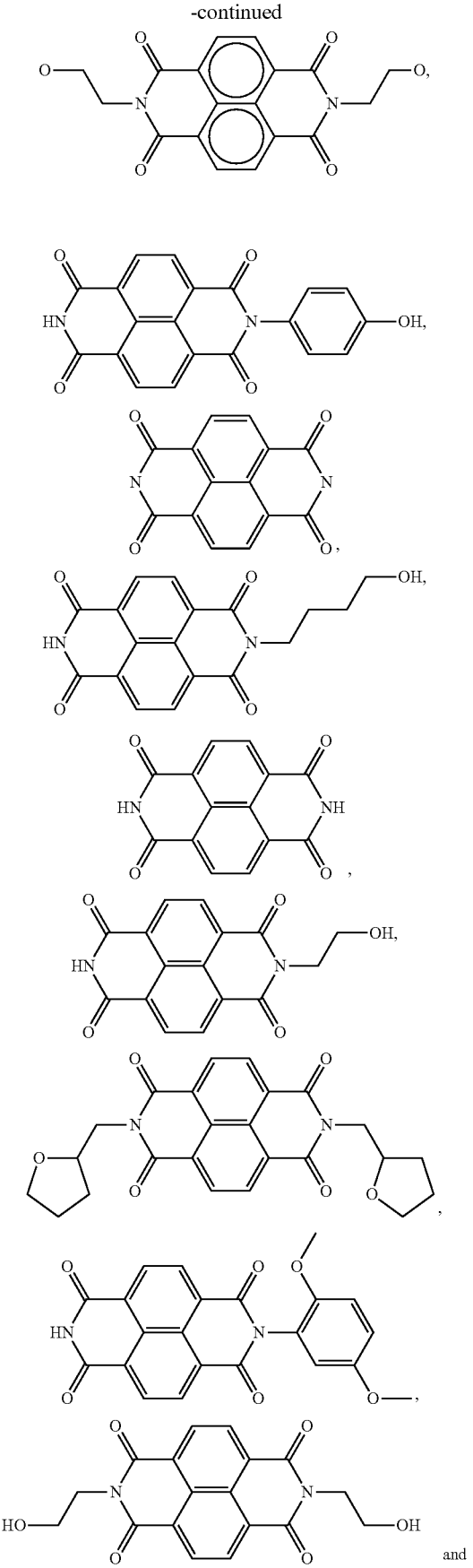

-continued

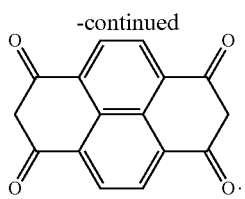

(5)

8. The method of claim 1, wherein said subject is an animal.

9. The method of claim 1, wherein said Gram-positive infection is an infection with *C. difficile*.

10. The method of claim 1, wherein at least one of $Y_1$ and $Y_2$=N, and the other of $Y_1$ and $Y_2$ is CH, CF, C-alkyl, C-alkoxy, C-alkoxyalkyl, C-carbocycle, C-heterocycle or N.

11. The method of claim 10, wherein $Y_2$ is N, CH, CF or C-alkyl and $Y_1$=N.

12. The method of claim 1, wherein $R_1$-$R_5$ are OMe, $C(O)CH_3$ or $C(O)$—$OCH_3$.

13. The method of claim 4, wherein n=m, $Q_1$=$P_1$, and $Q_2$=$P_2$.

14. The method of claim 1, wherein the bacteria are *Clostridium* species.

15. The method of claim 14, wherein the bacteria are *C. difficile*.

16. The method of claim 8, wherein the animal is a mammal.

17. The method of claim 16, wherein the mammal is a human.

* * * * *